United States Patent [19]
Riza

[11] Patent Number: 5,921,918
[45] Date of Patent: Jul. 13, 1999

[54] SURGICAL RETRACTOR

[76] Inventor: Erol D. Riza, 550 Riverside Dr., Rossford, Ohio 43460

[21] Appl. No.: 08/826,268

[22] Filed: Mar. 26, 1997

Related U.S. Application Data

[60] Provisional application No. 60/014,085, Mar. 26, 1996.

[51] Int. Cl.[6] ..................................................... A61B 17/00
[52] U.S. Cl. .......................... 600/204; 600/206; 600/226
[58] Field of Search .................................... 600/201, 202, 600/204, 206, 209, 226

[56] References Cited

U.S. PATENT DOCUMENTS

| | | |
|---|---|---|
| 1,708,578 | 4/1929 | Hyde . |
| 3,630,190 | 12/1971 | Baker . |
| 3,877,434 | 4/1975 | Ferguson et al. . |
| 4,002,169 | 1/1977 | Culper, II . |
| 4,230,123 | 10/1980 | Hawkins, Jr. . |
| 4,378,019 | 3/1983 | Yamada . |
| 4,517,965 | 5/1985 | Ellison ..................................... 600/204 |
| 4,616,656 | 10/1986 | Nicholson et al. . |
| 4,641,652 | 2/1987 | Hutterer et al. . |
| 4,779,616 | 10/1988 | Johnson . |
| 4,796,626 | 1/1989 | DeVries . |
| 4,874,375 | 10/1989 | Ellison ................................. 600/204 X |
| 4,935,008 | 6/1990 | Lewis, Jr. . |
| 5,106,369 | 4/1992 | Christmas . |
| 5,172,701 | 12/1992 | Leigh . |
| 5,217,024 | 6/1993 | Dorsey et al. . |
| 5,242,456 | 9/1993 | Nash et al. . |
| 5,250,054 | 10/1993 | Li . |
| 5,281,237 | 1/1994 | Gimpelson . |
| 5,289,817 | 3/1994 | Williams et al. ....................... 600/204 |
| 5,364,410 | 11/1994 | Failla et al. . |
| 5,387,227 | 2/1995 | Grice . |
| 5,405,354 | 4/1995 | Sarrett . |
| 5,450,842 | 9/1995 | Tovey et al. ......................... 600/204 X |
| 5,474,056 | 12/1995 | Laborie et al. ........................... 600/214 |
| 5,501,654 | 3/1996 | Failla et al. .............................. 600/204 |
| 5,501,692 | 3/1996 | Riza . |
| 5,512,037 | 4/1996 | Russell et al. ....................... 600/204 X |

FOREIGN PATENT DOCUMENTS 969254 10/1992 U.S.S.R. .

OTHER PUBLICATIONS

Product Brochure for RANFAC® Pneumoperitoneum Insufflation Needle (no date).
Catalog page for Suture Retriever, Copyright 1988 Acufex Microsurgical, Inc.
"Endoscopic Technique for ACL Reconstruction With Pro-Trac® Tibial Guide", Copyright 1991 Acufex Microsurgical, Inc.

*Primary Examiner*—Jeffrey A. Smith
*Attorney, Agent, or Firm*—MacMillan, Sobanski & Todd, LLC

[57] ABSTRACT

An instrument for facilitating the use of sutures in laparoscopic surgical procedures includes a hollow housing defining an internal cavity. A plunger extends within the cavity of the housing and is supported therein for relative sliding movement between first and second axial positions. A spring disposed within the cavity urges the plunger to the first axial position relative to the housing. A hollow introducer needle is secured to the housing and extends co-axially therefrom, terminating in an angled tip having a sharp point. An actuator tube is disposed within the introducer needle and is secured to the plunger for axial movement therewith relative to the housing. A flexible wire is disposed within portions of the actuator tube and is secured thereto for axial movement with the plunger in the introducer needle. The wire is resiliently predisposed to form a curved loop in a wire end thereof. When the plunger is in the first axial position, the wire end is withdrawn within the angled end of the introducer needle. When the plunger is moved to the second axial position, the wire end of the wire is extended outwardly from the angled end of the introducer needle. The wire end tends to form an open loop with a C-, J-, or S-shape when extended outwardly from the introducer needle.

19 Claims, 4 Drawing Sheets

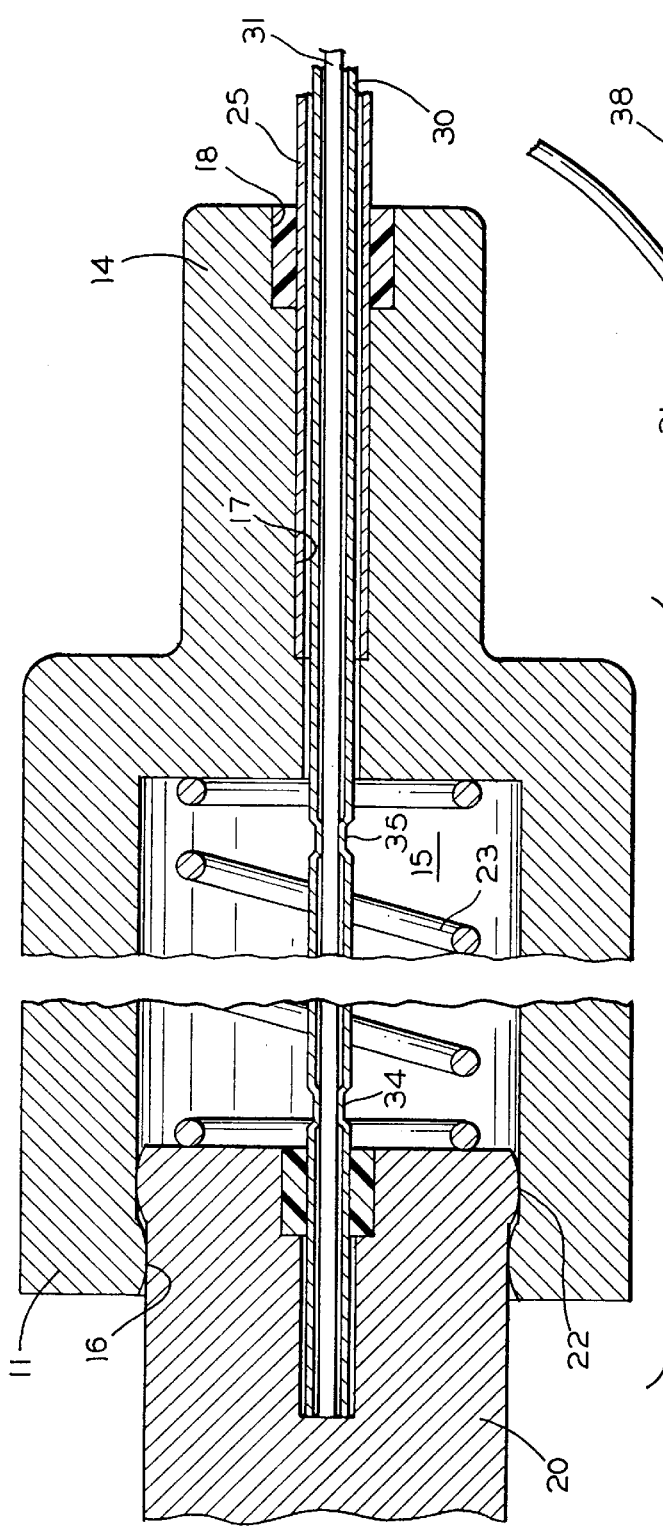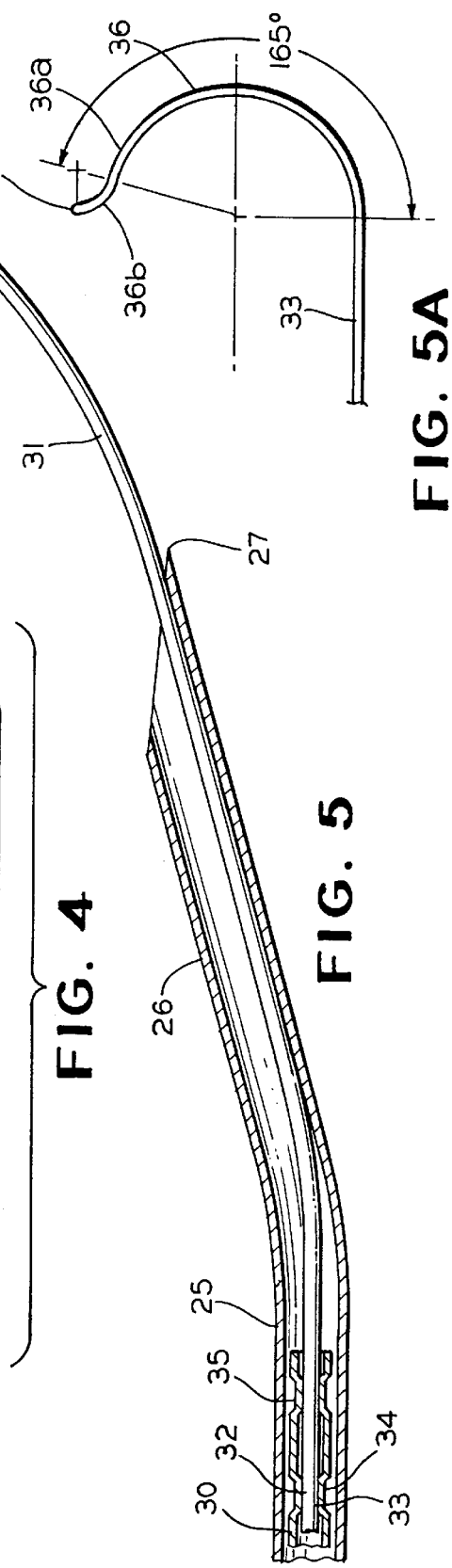

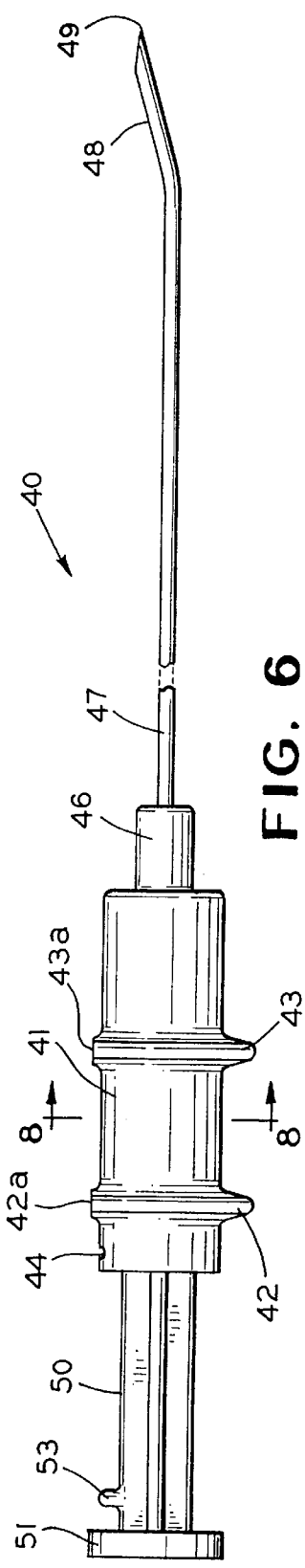
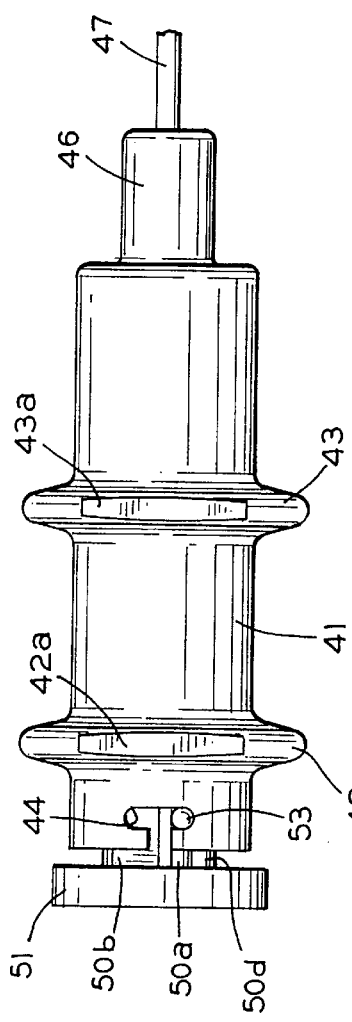
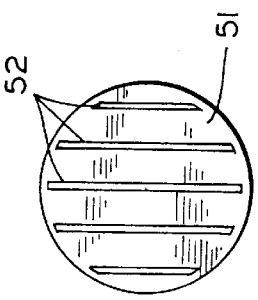

SURGICAL RETRACTOR

CROSS REFERENCE TO RELATED APPLICATIONS

This application claims the benefit of U.S. Provisional application Ser. No. 60/014,085, filed Mar. 26, 1996.

BACKGROUND OF THE INVENTION

This invention relates in general to surgical instruments and in particular to a surgical retractor for manipulating organs and other body tissue, as well as ligatures and surgical instruments, during laparoscopic. arthroscopic, and other similar surgical procedures.

Laparoscopic surgery is a relatively new operating technique which is much less invasive than conventional surgery and, therefore, may be performed using only a local anesthetic. Such laparoscopic surgery typically involves puncturing the abdominal wall and introducing an inert gas within the abdomen. The introduction of the inert gas expands the abdomen to facilitate access to the body parts requiring surgery and visual observation of the procedure. A hollow cylindrical tube, known as a cannula, is inserted into the puncture and is subsequently used as a conduit through which one or more elongated surgical instruments may be inserted within the abdomen. One type of surgical instrument which may be inserted through such a cannula is a surgical retractor. A surgical retractor is used to manipulate organs of other body tissue within the surgical site, either to move the body tissue out of the way of the surgeon, or to position the body tissue to a position required for the surgical procedure. Movement of a surgical retractor extending through a cannula is necessarily restricted by the relatively small diameter of the cannula and it may not be possible to cover the entire surgical site through a single cannula. If desired, a plurality of punctures may be formed through the abdominal wall to facilitate the use of several surgical retractors at various required locations about the surgical site.

However, the use of small punctures to introduce cannulas results in a great reduction in tissue trauma associated with gaining access to the surgical site as compared to traditional open surgical techniques. However, abdominal wall blood vessels may be injured and cause significant bleeding during the puncturing of the abdominal wall to insert a cannula, since even small diameter cannulas are of a relatively large diameter compared to a blood vessel in order to accommodate the typical surgical retractor of the past. For this reason, and to minimize overall surgical trauma, surgeons try to limit the number of cannulas used during surgery, and thus may attempt to operate a retractor from an awkward position rather than introduce a cannula to a new location, with the attendant risks and additional trauma. Thus, it would be desirable to provide an improved surgical retraction instrument for in laparoscopic surgical procedures which do not require insertion through a large diameter cannula.

SUMMARY OF THE INVENTION

This invention relates to a surgical retractor instrument for manipulating body tissue, ligatures and surgical instruments in laparoscopic surgical procedures. The surgical retractor includes a generally hollow cylindrical housing which is formed having a pair of circumferential flanges formed thereabout. The housing is formed having an internal cylindrical cavity which defines an internal diameter and extends from an opened end to a closed end. A plunger having an enlarged head extends within the cavity of the housing and is supported therein for relative sliding movement between first and second axial positions. A coiled spring disposed within the cavity urges the plunger to the first axial position relative to the housing. A tubular metallic introducer needle is secured to the housing and extends co-axially therefrom, terminating in an angled tip having a sharp point. A tubular metallic actuator tube is disposed within the introducer needle and is secured to the plunger for axial movement therewith relative to the housing. A flexible metallic wire is disposed within portions of the actuator tube and is secured thereto for axial movement with the plunger. When the plunger is in the the second axial position, the wire end of the wire is extended outwardly from the angled end of the introducer needle. The wire end of is resiliently predisposed to form a C-, J-, or S-shaped curve, when extended outwardly from the introducer needle. When the plunger is in the first axial position, the wire end of the wire is straightened and is retracted into the angled end of the introducer needle assuming the general shape of the surrounding portion of the introducer needle.

Various objects and advantages of this invention will become apparent to those skilled in the art from the following detailed description of the preferred embodiments, when read in light of the accompanying drawings.

BRIEF DESCRIPTION OF THE DRAWINGS

FIG. 4 is an enlarged fragmentary sectional elevational view of the first and second ends of the housing of the surgical retractor illustrated in FIG. 2.

FIG. 5 is an enlarged fragmentary sectional elevational view of the tip of the surgical retractor illustrated in FIG. 2.

FIG. 5A is an enlarged view of the wire end of the wire illustrated in FIG. 5.

FIG. 6 is a side elevational view of a second embodiment of a laparoscopic surgical retractor in accordance with this invention, wherein the plunger of the surgical retractor is shown in a first axial position relative to the housing.

FIG. 7 is an enlarged top plan view of a portion of the surgical retractor illustrated in FIG. 6.

FIG. 8 is a sectional elevational view taken along the line 8—8 of FIG. 6.

FIG. 9 is an end elevational view of the enlarged head of the plunger illustrated in FIG. 6.

DETAILED DESCRIPTION OF THE PREFERRED EMBODIMENTS

Figure 1:
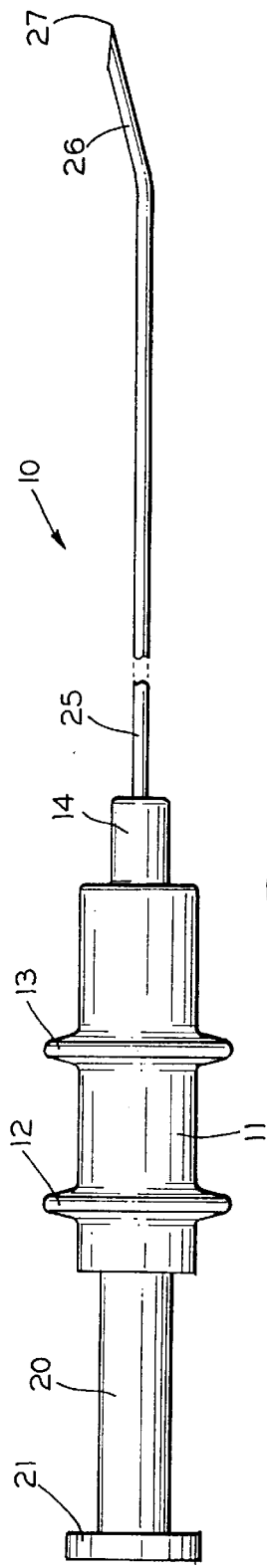
FIG. 1 is a side elevational view of a first embodiment of a laparoscopic surgical retractor in accordance with this invention, wherein the plunger of the surgical retractor is shown in a first axial position relative to the housing.
Figure 2:
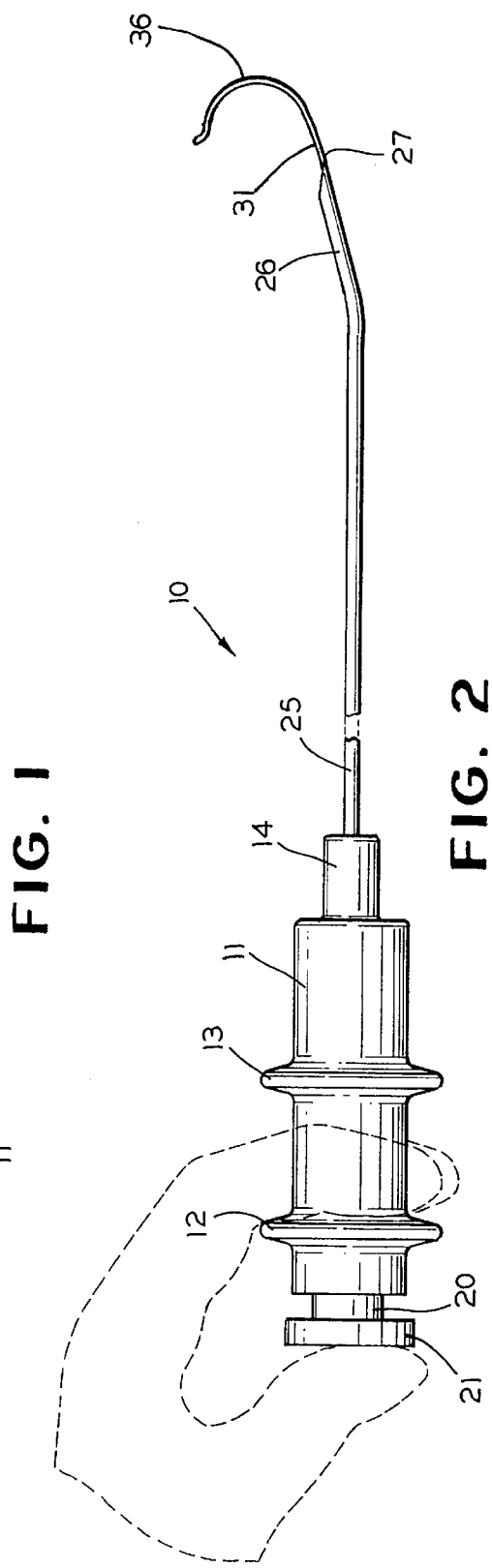
FIG. 2 is a side elevational view similar to FIG. 1, wherein the plunger of the surgical retractor is shown in a second axial position relative to the housing.
Figure 3:
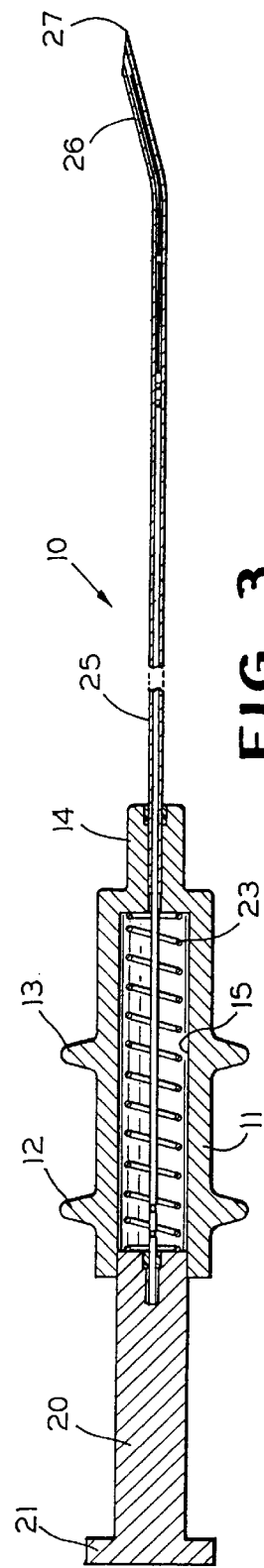
FIG. 3 is a sectional elevational view of the surgical retractor illustrated in FIG. 1.

Referring now to the drawings, there is illustrated in FIGS. 1 through 3 a first embodiment of a laparoscopic surgical retractor, indicated generally at 10, in accordance with this invention. The surgical retractor 10 includes a generally-hollow cylindrical housing 11 which is formed having a pair of circumferential flanges 12 and 13 formed thereabout. The first circumferential flange 12 is located adjacent to a first end of the housing 11, while the second circumferential flange 13 is located adjacent to a second end of the housing 11. Thus, the flanges 12 and 13 are axially spaced apart from one another, preferably by a distance of about three-fourths of one inch. As will be explained further below, the flanges 12 and 13 function as finger grips for grasping the housing 11. The housing 11 further includes a co-axial extension 14 provided at the second end thereof. The extension 14 is smaller in diameter than the housing 11 and is preferably formed integrally therewith. Preferably, the entire housing 11 is formed from a molded plastic material.

Referring now to FIGS. 3 and 4, the internal structure of the housing 11 is illustrated in detail. As shown therein, the housing 11 is formed having an internal cylindrical cavity 15. The cavity 15 defines an internal diameter and extends from an opened end at the first end of the housing 11 to a closed end adjacent the second end of the housing 11. A small radially inwardly extending ridge 16 is formed about the circumference of the opening defined at the first end of the housing 11 by the cavity 15. The purpose of this ridge 16 will be explained below. A co-axial passageway 17 extends from the cavity 15 through the extension 14 to a co-axial recess 18 formed in the second end of the housing 11. The purposes of the passageway 17 and the recess 18 will be explained below.

The surgical retractor 10 also includes a plunger 20 having an enlarged head 21 formed at one end. The plunger 20 extends within the cavity 15 of the housing 11. The outer diameter of the plunger 20 is slightly smaller than the inner diameter of the cavity 15. Thus, the plunger 20 is supported within the housing 11 for relative axial sliding movement. As best shown in FIG. 4, a small radially outwardly extending ridge 22 is formed about the end of the plunger 20 opposite the head 21. The purpose of the ridge 22 will be explained below. As with the housing 11, the entire plunger 20 is preferably formed from a molded plastic material.

A coiled spring 23 or other resilient structure is disposed within the cavity 15. The ends of the spring 23 react against the inner end of the plunger 20 (adjacent to the ridge 22) and the closed end of the cavity 15. Thus, the spring 23 urges the plunger 20 to a first axial position relative to the housing 11, as shown in FIGS. 1 and 4. When in this position, the inner ridge 16 formed on the housing 11 engages the outer ridge 22 formed on the plunger 20. As a result, the plunger 20 is not ejected from the housing 11 under the urging of the spring 23. However, the plunger 20 can be removed from the housing 11 by manually applying a somewhat greater force, so as to compress the ridges 16 and 22. The plunger 20 may be moved to a second axial position within the housing 11 against the urging of the spring 23 by applying an appropriate force thereto. Typically, this force will be applied by squeezing with the fingers and thumb of a hand, such as shown in dotted lines in FIG. 2.

The surgical retractor 10 further includes a tubular metallic introducer needle 25. The introducer needle 25 is secured to the axial extension 14 of the housing 11 and extends co-axially therefrom. Referring to FIG. 4, a first end of the introducer needle 25 extends through the recess 18 into a press fit relationship within the passageway 17 of the extension 14. The recess 18 may then be filled with an adhesive material to secure the introducer needle 25 to the housing 11. However, the first end of the introducer needle 25 may be fixed to the housing 11 by any suitable means, such as by integrally molding the housing 11 about the needle 25 or by a mechanical fastener. The second end of the introducer needle 25 is preferably (but not necessarily) angled, as shown at 26, relative to the longitudinal axis defined by the housing 11 at any desired angle. Also, the second end 26 of the introducer needle 25 is preferably provided with a sharp point 27.

The surgical retractor 10 further includes an elongated tubular metallic actuator tube 30 which is disposed within the introducer needle 25. A first end of the actuator tube 30 is secured to the inner end of the plunger 20 by any suitable means, such as those described above for securing the first end of the introducer needle 25 to the housing 11. Thus, the actuator tube 30 is secured to the plunger 20 for axial movement therewith relative to the housing 11. The actuator tube 30 extends through the cavity 15, the passageway 17, and into a portion of the introducer needle 25.

A flexible metallic wire 31 is disposed within portions of the actuator tube 30. As best shown in FIGS. 4 and 5, the wire 31 is located within the intermediate portion of the actuator tube 30. The wire 31 is secured to the actuator tube 30. In the illustrated embodiment, the actuator tube 30 is crimped about the wire 31 at two locations 34 and 35 to effect the connection therebetween. However, any conventional means may be used to connect the wire 31 to the actuator tube 30. As a result, the wire 31 is secured to the actuator tube 30 for axial movement therewith when the plunger 20 is moved as described above. As shown in FIG. 5A, the wire 31 has a resilient wire end 36 which has a first portion 36a tending to form a generally C- or J-shaped curve or other suitable shaped end which is useful on a retractor. In one preferred embodiment the first portion 36a of the wire end 36 forms a C- shaped curve with an arc of about a 165 degrees. The wire 31 preferably ends in a slight bend forming an end portion 36b which has an arcuate shape and is curved in a contrary direction to the first portion 36a of the wire end 36, such that the first portion 36a and the end portion 36b form an S-shaped curve. The wire 31 terminates in a tip 38 which will preferably be rounded over to minimize the chance of inadvertent punctures. The wire 31 may suitably be comprised of a shape memory alloy, such as a Nickel-Titanium alloy (NiTi), for superior shape holding properties.

When the plunger 20 is in the first axial position illustrated in FIGS. 1, 3, and 4, the actuator tube 30 is located in a retracted position within the introducer needle 25. Thus, the wire 31 is also located in a retracted position within the introducer needle 25. As a result, the wire end 36 of the wire 31 is withdrawn within the angled end 26 of the introducer needle 25. When this occurs, the wire end 36 is resiliently deformed to assume the general shape of the surrounding portion of the introducer needle 25. If the surrounding portion of the introducer needle 25 is straight, then the wire end 36 will be generally straight.

When the plunger 20 is moved to the second axial position illustrated in FIGS. 2 and 5, the actuator tube 30 is moved to an extended position relative to the introducer needle 25. Thus, the wire 31 is also moved to an extended position relative to the introducer needle 25. As a result, the wire end 36 of the wire 31 is extended outwardly from the angled end 26 of the introducer needle 25. When this occurs, the resilient wire end 36 assumes the curved configuration illustrated in FIG. 5A.

Of course, it will normally be desirable to be able to have the wire end 36 of the wire 31 remain in an extended position without the surgeon having to continuously apply pressure with his or her thumb to the plunger 20. Therefore, FIGS. 6 through 9 illustrate a second embodiment of a laparoscopic surgical retractor, indicated generally at 40, in accordance with this invention. The surgical retractor 40 includes a generally hollow cylindrical housing 41 generally similar in structure to the housing 11 of the first embodiment described above. The housing 41 is formed having a pair of circumferential flanges 42 and 43 formed thereabout. The first circumferential flange 42 is located adjacent to a first end of the housing 41, while the second circumferential flange 43 is located adjacent to a second end of the housing 41. Thus, the flanges 42 and 43 are axially spaced apart from one another, preferably by a distance of about three-fourths of one inch. As in the first embodiment described above, the flanges 42 and 43 function as finger grips for grasping the housing 41. The flanges 42 and 43 are formed having respective flats 42a and 43a in the upper portions thereof, for a purpose which will be explained below.

The upper portion of the housing 41 is formed having a generally T-shaped slot 44. The stem portion of the T-shaped slot 44 extends from the first end of the housing 41 axially toward the first circumferential flange 42. The cross portion of the T-shaped slot 44 extends transversely from the end of the stem portion. The slot 44 is formed completely through the housing 41 from the exterior surface thereof to an internal cavity 45 (see FIG. 8) defined therein. The purpose of the slot 44 will be discussed below. As with the housing 11 described above, the housing 41 also includes a co-axial extension 46 provided at the second end thereof. The extension 46 is smaller in diameter than the housing 41 and is preferably formed integrally therewith from a molded plastic material. Also, an introducer needle 47, similar to the introducer needle 25 discussed above, is secured to the axial extension 47 of the housing 41 and extends co-axially therefrom.

As in the first embodiment discussed above, the introducer needle 47 of the surgical retractor 40 includes an angled end portion 48 and a sharp tip 49. The angled end portion 48 preferably extends upwardly in alignment with the upper flats 42a and 43a respectively formed on the flanges 42 and 43. Thus, the flats 42a and 43a provide the user of the surgical retractor 40 with a tactile indication of the relative orientation of the angled end 48 of the introducer needle 47.

As best shown in FIG. 8, and similar to the internal cavity 15 described above, the internal cavity 45 of the housing 41 defines an internal diameter and extends from an opened end at the first end of the housing 41 to a closed end adjacent the second end of the housing 41. Unlike the cavity 15, however, an axially extending recess 45a is formed in the upper portion of the inner surface of the housing 41. The recess 45a extends from the open end of the housing 41 throughout most or all of the cavity 45. The axially extending sides of the recess 45a define an arc relative to the longitudinal axis of the housing 41. Preferably, the magnitude of this arc is approximately twenty-eight degrees. The purpose of the recess 45a will be discussed below.

The surgical retractor 40 also includes a plunger 50 having an enlarged head 51 formed at one end. As best shown in FIG. 9, the head 51 is formed having a plurality of parallel raised ribs 52 on the outer face thereof. The purpose of the raised ribs 52 will be discussed below. The plunger 50 extends within the cavity 45 of the housing 41. As best shown in FIG. 8, the plunger 50 is formed generally in the shape of a cross having four radially outwardly extending web portions 50a, 50b, 50c, and 50d. The ends of the web portions 50a, 50b, 50c, and 50d abut the inner surface of the housing 41 to support the plunger 50 therein for relative axial sliding movement. The web portion 50a extends radially outwardly slightly further than the remaining web portions 50b, 50c, and 50d. As a result, the web portion 50a extends into the recess 45a formed in the inner surface of the housing 41. The cooperation of the web portion 50a with the recess 45a limits the ability of the plunger 50 to rotate relative to the housing 41 to the arc defined by the longitudinal sides of the recess 45a.

An upstanding pin 53 is provided on the outer end of the web portion 50a adjacent to the enlarged head 51 of the plunger 50. The pin 53 is preferably formed as an integral part of the plunger 50. The pin 53 is sized to fit into the slot 44 formed in the housing 41, as illustrated in FIG. 7, when the plunger 50 is moved to the second axial position relative to the housing 41. The cooperation of the web portion 50a of the plunger 50 with the recess 45a of the housing 41 maintains the pin 53 in axial alignment with the stem portion of the slot 44. As a result, the plunger 50 can easily be depressed within the housing 41 to the second axial position.

In some instances, it may be desirable to lock the plunger 50 in the second axial position. To accomplish this, the plunger 50 is rotated relative to the housing 41 so as to cause the pin 53 to be moved into the cross portion of the slot 44, as shown in FIG. 7. This relative rotation movement is facilitated by the raised ribs 52 provided on the enlarged head 51 of the plunger 50. The ribs 52 provide for increased frictional engagement by the thumb of the user for accomplishing this relative rotational movement. Preferably, rotation of approximately thirteen degrees will be sufficient to move the pin 53 into the cross portion of the slot 44. The remaining portions of the surgical retractor 40 are identical to the surgical retractor 10 described above and, therefore, require no further explanation.

The surgical retractor instruments 10 and 40 are preferably utilized to manipulate organs and other body tissue in a laparoscopic or similar surgical procedure. To accomplish this, the housing 11 is supported by the index and middle fingers of one hand (shown in dotted lines in FIG. 2) extending between the flanges 12 and 13. The thumb of the same hand is used to selectively depress the plunger 20 for movement between the first and second axial positions relative to the housing 11. When the plunger 20 is depressed, the wire end 36 is extended from the angled end 26 of the introducer needle 25 and expands into the illustrated C-shaped curve 36. Of course, the wire 31 may be manufactured so that the wire end 36 will resiliently assume any curved shape suitable for use on a retractor when extended from the introducer needle. When so extended and expanded, the wire end 36 can be used to manipulate body tissue, such as moving the body tissue out of the way or positioning the body tissue to a position required for the surgical procedure. The surgical retractor 40 operates in generally the same manner as the surgical retractor 10, but is further provided with the slot 44 and the pin 53 for selectively maintaining the wire end 36 of the wire 31 in the extended position.

Figure 11:
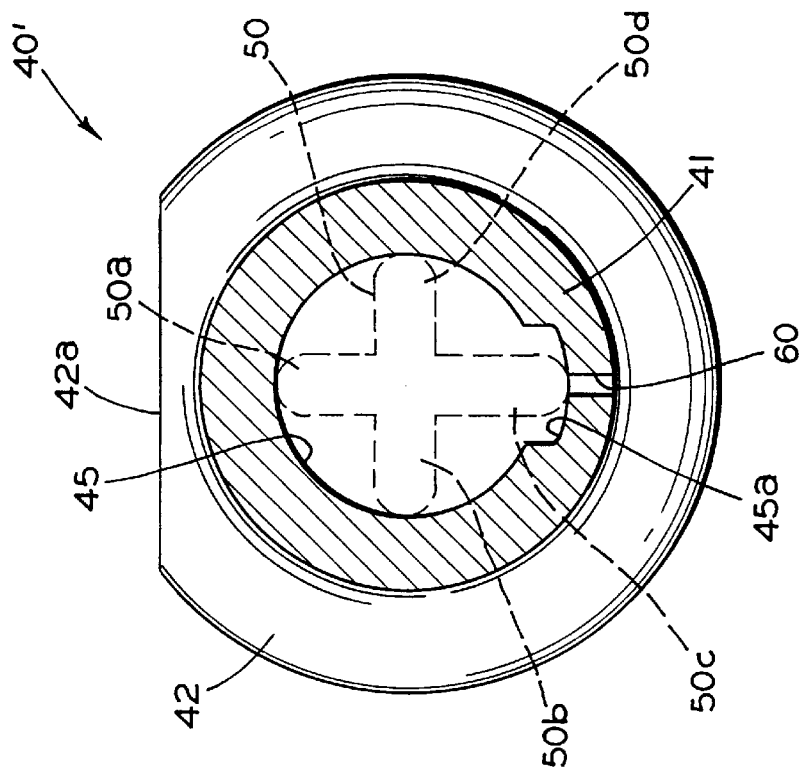
FIG. 11 is a view taken along the line 11—11 of FIG. 10.
Figure 10:
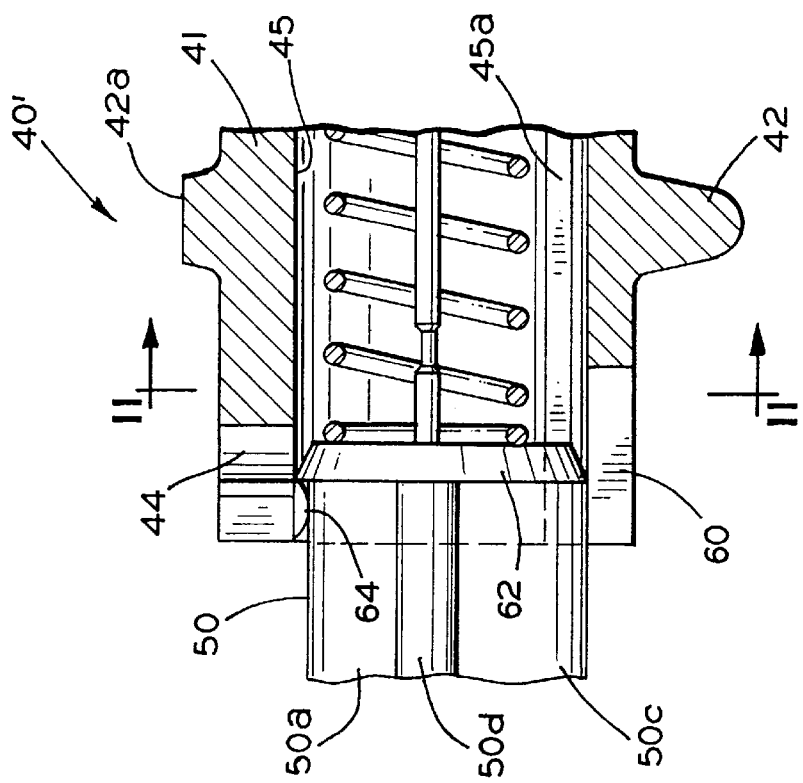
FIG. 10 is a side sectional view of another embodiment.

FIGS. 10 and 11 illustrate an alternate embodiment of a laparoscopic surgical retractor indicated generally at 40'. The surgical retractor 40' is generally similar in structure to the surgical retractor 40 and like reference numbers will be used to refer to similar structures. One difference of the surgical retractor 40' is that the axially extending recess 45a is formed in the lower portion (as viewed in FIG. 10) of the inner surface of the housing 41 rather than in the upper portion as in the surgical retractor 40. To accommodate the difference in the location of the recess 45a, the plunger 50 is modified so that the web portion 50c extends more radially outwardly than the web portions 50a, 50b, and 50d. The web portion 50c cooperates with the recess 45a to limit the ability of the plunger 50 to rotate relative to the housing 41. This is most clearly seen in FIG. 11, wherein the position of the plunger 50 when moved further into the internal cavity 45 of the housing 41 is shown in phantom lines.

An axially extending slot 60 is formed through the lower portion of the housing 41. The slot 60 allows the adjacent portions of the housing 41 to resiliently deflect during assembly. During assembly, a small radially extending ridge 62 formed about the end of the plunger 50 axially passes by a small radially inwardly extending ridge 64 formed about the majority of the circumference of the opening at the first end of the housing 41. The ridges 62 and 64 function similarly to the ridges 22 and 16 of the surgical retractor 10. Of course, the surgical retractors 10 and 40 could be provided with slots similar to the slot 60.

Referring again to FIG. 5A, it will be appreciated that the radius and extent of the arc of the first portion 36a and the end portion 36b may suitably be changed from what is shown in the Figures. For example, in another embodiment of the laparoscopic surgical retractor 10, the first portion 36a of the wire end 36 preferably forms a C-shaped curve with an arc within the range from about 105 degrees to about 125 degrees. The first portion 36a and the end portion 36b cooperate to form a gently sloping S-curve.

In accordance with the provisions of the patent statutes, the principle and mode of operation of the present invention have been explained and illustrated in its preferred embodiments. However, it must be understood that the present invention may be practiced otherwise than as specifically explained and illustrated without departing from its spirit or scope.

What is claimed is:

1. A surgical retractor comprising:
   a hollow housing defining an internal cavity;
   a plunger extending within said cavity of said housing for relative movement between first and second axial positions;
   an introducer needle secured at a first end to said housing and extending therefrom to a second end;
   a wire having a wire end, said wire being operatively coupled to said plunger for movement with said plunger in said introducer needle, said wire end being extended outwardly from said second end of said introducer needle when said plunger is in said second axial position, said wire end resiliently assuming a curved shape when thus extended, said wire end being retracted into said introducer needle when said plunger is in said first axial position, said wired end being resiliently deformed to assume the general shape of the surrounding introducer needle when thus retracted; and
   a spring disposed within the internal cavity of said housing for reacting between said housing and said plunger for urging the plunger toward the first axial position.

2. The surgical retractor defined in claim 1 further including a circumferential flange formed about said housing.

3. The surgical retractor of claim 1 further including means for locking said plunger in said second axial position.

4. The surgical retractor defined in claim 3 wherein said means for locking includes a slot formed in said housing and a pin formed on said plunger, said pin cooperating with said slot to lock said plunger in said second axial position.

5. The surgical retractor defined in claim 1 wherein said second end of said introducer needle extends at an angle relative to a longitudinal axis defined by said housing.

6. The surgical retractor of claim 5 further including means for providing a tactile indication of said angle of said second end of said introducer needle.

7. The surgical retractor of claim 6 wherein said means for providing a tactile indication includes a flange extending outwardly from said housing having a flat formed thereon.

8. The surgical retractor defined in claim 1 further including means for limiting relative rotation between said plunger and said housing.

9. The surgical retractor defined in claim 8 wherein said means for limiting relative rotation includes a recess formed in an inner surface of said housing and a web member extending radially outwardly from said plunger into cooperation with said recess.

10. The surgical retractor defined in claim 1 further including means for preventing said plunger from being ejected from said housing.

11. The surgical retractor defined in claim 10 wherein said means for preventing includes an outwardly extending ridge formed on an end of said plunger and a cooperating inwardly extending ridge formed on said housing.

12. The surgical retractor defined in claim 1 further including an actuator member disposed within said introducer needle and connected between said plunger and said wire for axial movement between said first and second axial positions.

13. The surgical retractor defined in claim 1 wherein said wire end of said wire includes a first portion curved into an open loop shape when said wire end is extended outwardly from said second end of said introducer needle when said plunger is in said axial position, said open loop including an end portion curved in a contrary direction to said first portion.

14. The surgical retractor defined in claim 1 wherein said wire end is comprised of a shape memory alloy.

15. The surgical retractor defined in claim 14 wherein said wire end is comprised of a Nickel-Titanium alloy.

16. The surgical retractor defined in claim 1 wherein said wire end of said wire terminates in a rounded tip.

17. A surgical retractor comprising:
   a hollow housing defining an internal cavity, said housing including a slot formed therein;
   a plunger extending within said cavity of said housing for relative movement between first and second axial positions, said plunger including a pin extending therefrom, said pin on said plunger cooperating with said slot in said housing to lock said plunger in said second axial position;
   an introducer needle secured at a first end to said housing and extending therefrom; and
   a wire having a wire end, said wire being operatively coupled to said plunger for movement with said plunger in said introducer needle, said wire end extending outwardly from said second end of said introducer needle and resiliently assuming a curved shape when said plunger is in said second axial position, said wire end retracting into said introducer needle and resiliently deformed to assume the general shape of the surrounding introducer needle when said plunger is in said first axial position.

18. A surgical retractor comprising:
   a hollow housing defining an internal cavity;
   a plunger extending within said cavity of said housing for relative movement between first and second axial positions;
   an introducer needle secured at a first end to said housing and extending therefrom to a second end, said second end extending at an angle relative to a longitudinal axis defined by said housing;

a flange extending outwardly from said housing having a flat formed thereon for providing a tactile indication of said angle of said second end of said introducer needle; and a wire having a wire end, said wire being operatively coupled to said plunger for movement with said plunger in said introducer needle, said wire end extending outwardly from said second end of said introducer needle and resiliently assuming a curved shape when said plunger is in said second axial position, said wire end retracting into said introducer needle and resiliently deformed to assume the general shape of the surrounding introducer needle when said plunger is in said first axial position.

19. A surgical retractor comprising:

a hollow housing defining an internal cavity, said housing including a recess formed in an inner surface thereof;

a plunger extending within said cavity of said housing for relative movement between first and second axial positions, said plunger including a web member extending radially outwardly from said plunger, said web member of said plunger cooperating with said recess formed in said housing to limit relative rotation between said plunger and said housing;

an introducer needle secured at a first end to said housing and extending therefrom to a second end; and a wire having a wire end, said wire being operatively coupled to said plunger for movement with said plunger in said introducer needle, said wire end extending outwardly from said second end of said introducer needle and resiliently assuming a curved shape when said plunger is in said second axial position, said wire end retracting into said introducer needle and resiliently deformed to assume the general shape of the surrounding introducer needle when said plunger is in said first axial position.

\* \* \* \* \*